(12) United States Patent
Viker

(10) Patent No.: US 8,147,525 B2
(45) Date of Patent: Apr. 3, 2012

(54) BONE ANCHOR ASSEMBLY AND METHODS OF USE

(75) Inventor: Thomas O. Viker, Arden Hills, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 496 days.

(21) Appl. No.: 12/341,247

(22) Filed: Dec. 22, 2008

(65) Prior Publication Data

US 2010/0160965 A1 Jun. 24, 2010

(51) Int. Cl.
*A61B 17/88* (2006.01)
(52) U.S. Cl. .................... 606/279; 606/264; 128/898
(58) Field of Classification Search .......... 606/264–279, 606/300–321, 99, 86 A; 128/898
See application file for complete search history.

(56) References Cited

U.S. PATENT DOCUMENTS

| | | | |
|---|---|---|---|
| 5,690,630 A | 11/1997 | Errico et al. | |
| 5,776,135 A | 7/1998 | Errico et al. | |
| 6,063,089 A | 5/2000 | Errico et al. | |
| 6,187,005 B1 * | 2/2001 | Brace et al. | 606/264 |
| 7,842,072 B2 * | 11/2010 | Dawson | 606/263 |
| 2006/0235389 A1 * | 10/2006 | Albert et al. | 606/61 |
| 2006/0241600 A1 | 10/2006 | Ensign et al. | |
| 2008/0140075 A1 | 6/2008 | Ensign et al. | |

* cited by examiner

*Primary Examiner* — Eduardo C Robert
*Assistant Examiner* — Christina Negrelli
(74) *Attorney, Agent, or Firm* — Seager Tufte & Wickhem LLC

(57) ABSTRACT

A method of treating the spine of a patient involves inserting anchors into vertebrae and connecting the anchors to a longitudinal member via housings. After insertion of the anchors, the housings containing a longitudinal member are positioned over the anchors and fastened.

23 Claims, 16 Drawing Sheets

BONE ANCHOR ASSEMBLY AND METHODS OF USE

BACKGROUND

The disclosure relates to a bone anchor assembly and method of using the assembly to retain bone portions, such as vertebrae of a spinal column, in a desired spatial relationship. The assembly for retaining vertebrae of a spinal column in a desired spatial relationship may include two or more bone anchors engageable with vertebrae of the spinal column, a longitudinal member extendable along the spinal column, and two or more housings connecting the longitudinal member and the bone anchor.

SUMMARY

The disclosure is directed to several alternative designs and methods of using medical device structures and assemblies. One embodiment includes a method of treating the spine of a patient, including providing two or more anchors for insertion into a plurality of adjacent vertebrae, each anchor having a head and a shaft, providing a housing for each anchor, each housing having a first passage extending longitudinally therethrough between an upper opening and a lower opening, a second passage transverse to the first passage and configured to receive a longitudinal member, and a side opening configured to receive the anchor head. The method also involves providing two or more housings for positioning onto a longitudinal member, the longitudinal member extending through the second passages in the housings. The longitudinal member is configured for positioning adjacent the anchors such that each housing is adjacent an anchor head, the housings are configured to slide onto the anchor heads with the anchor heads being received in the side openings, and the housings being securable to the anchor heads.

Another embodiment of a method for treating the spine of a patient, includes providing at least one access device for insertion through a first incision in the skin of the patient, the access device having a proximal end and a distal end and a path extending therebetween, the access device being advanced until the distal end is adjacent at least first and second vertebral target sites, providing two or more anchors for insertion through the access device, and securing the anchors to the patient's vertebrae at the first and second vertebral target sites, each anchor having a head and a shaft, the shaft being configured for securing to the vertebra. The method also involves providing a longitudinal member and two or more housings, the longitudinal member configured for insertion through two or more housings, each housing having a first passage extending longitudinally therethrough between an upper opening and a lower opening, a second passage transverse to the first passage and configured to receive the longitudinal member, and a side opening configured to receive the anchor head, inserting the longitudinal member and housings through the access device until a distal end of the longitudinal member is adjacent the first target site, advancing the distal end of the longitudinal member to the second target site, until a proximal end of the longitudinal member is adjacent the first target site, the distal end of the longitudinal member is adjacent the second target site, and each housing is adjacent an anchor head, sliding each housing onto an anchor head such that the anchor head enters the side opening, and securing the housings and longitudinal member to the anchor heads.

The above summary of some example embodiments is not intended to describe each disclosed embodiment or every implementation of the invention.

DETAILED DESCRIPTION

Various embodiments of apparatus and methods are described herein. The apparatus and methods may be used in minimally invasive or percutaneous procedures, and may also be used in conventional, open, or semi-open procedures. The apparatus may be used in fixation, fusion, compression, and/or distraction procedures.

Figure 1:
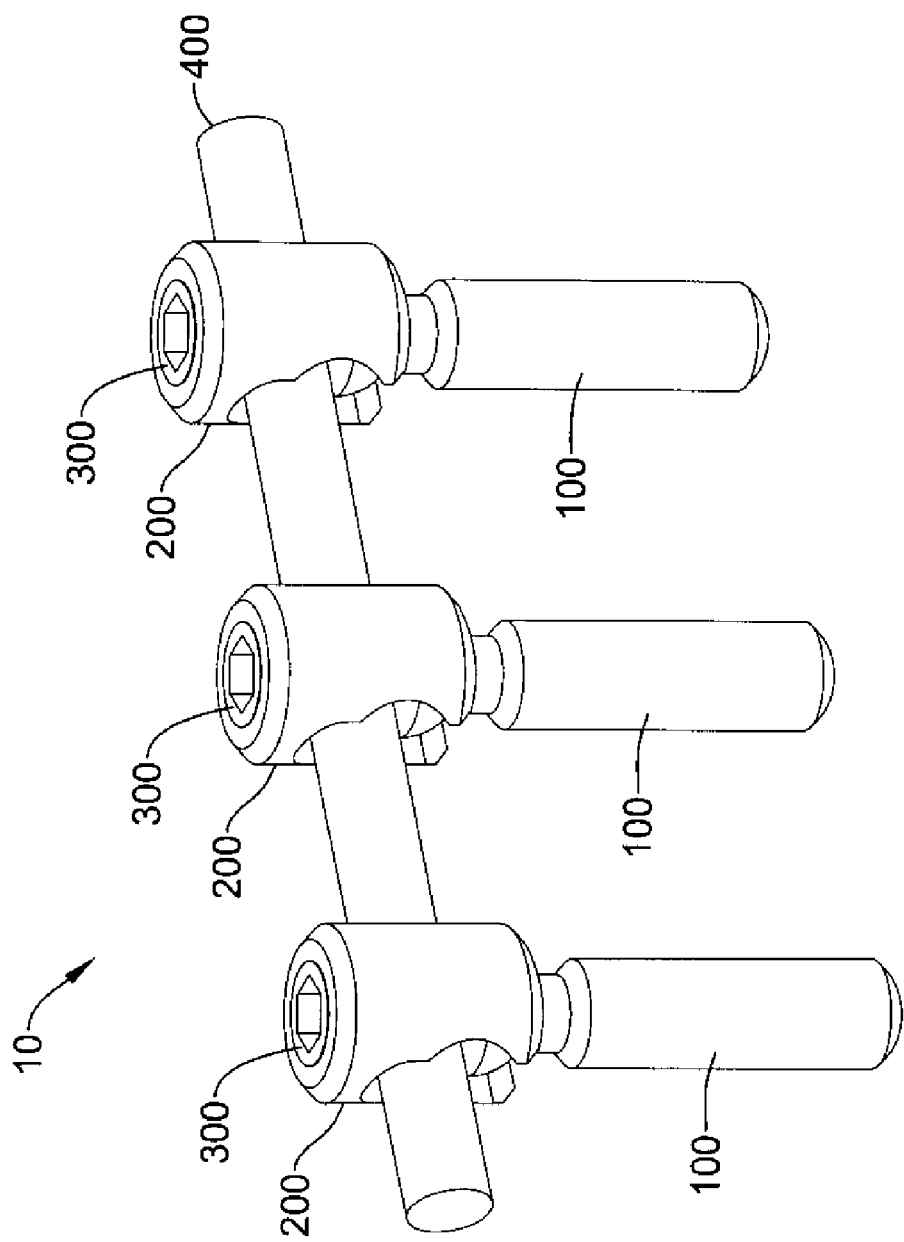
FIG. 1 is a perspective view of three bone anchors assembled on a longitudinal member in accordance with an embodiment of the present invention.

Referring now to the drawings wherein like reference numerals refer to like elements throughout the several views, FIG. 1 is a perspective view of an embodiment of a bone anchor assembly 10. The assembly 10 as shown in FIG. 1 includes three anchors 100 made of a suitable biocompatible material, each connected to a longitudinal member 400 by a housing 200 and fastener 300. Any number of anchors 100 may be connected to the longitudinal member 400 to achieve a bone anchor assembly 10 suitable for connecting to a desired number of vertebrae. The anchors 100 are inserted into adjacent vertebrae, and once connected to a longitudinal member 400, the assembly is used to modify and/or maintain the orientation of the vertebrae.

Figure 2:
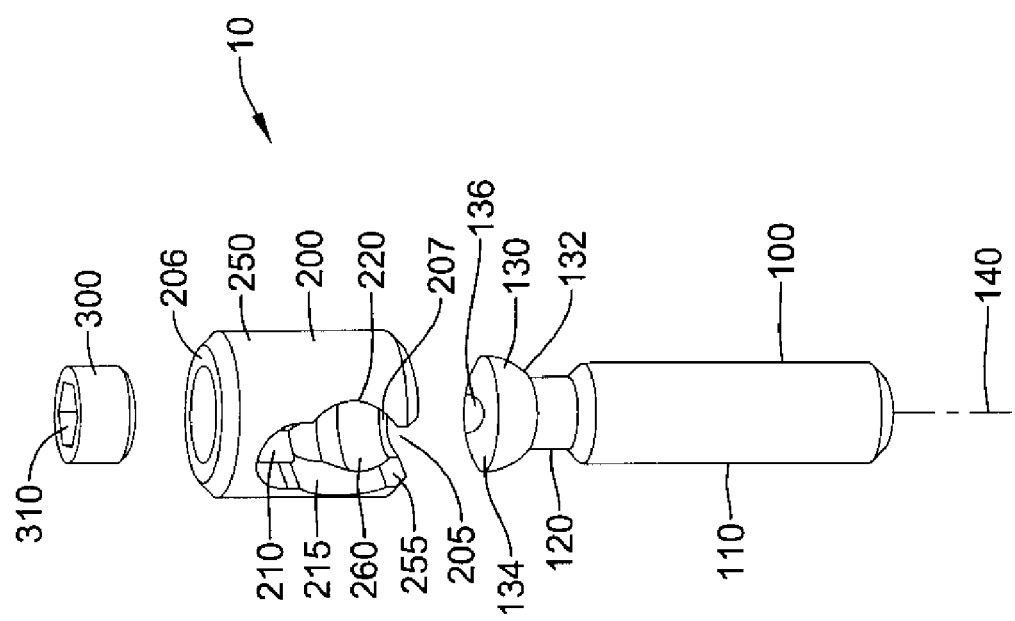
FIG. 2 is an exploded perspective view of a single bone anchor assembly.
Figure 3:
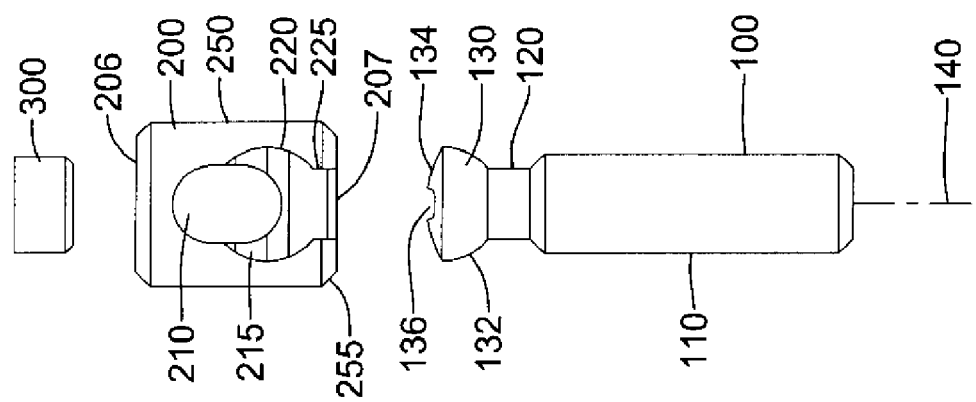
FIG. 3 is a front view of the bone anchor assembly of FIG. 2.

Each anchor 100 includes a shaft 110, a neck 120, and a head 130. The anchors 100 each have a longitudinal axis 140 (FIGS. 1-3). In some embodiments, the anchor has a threaded shaft (not shown). The anchor 100 may be cannulated for implantation over a guidewire. The head 130 of the anchor 100 has an upper surface 134, which may be part spherical, flat, concave, convex, or any other shape configured to receive a longitudinal member 400. The head 130 has a bottom part spherical surface 132 and an opening 136 on the upper surface 134 (FIGS. 2, 3). The opening 136 is sized and configured to receive a tool (not shown) that applies force to the anchor 100 to insert the anchor into a vertebra.

Figure 15:
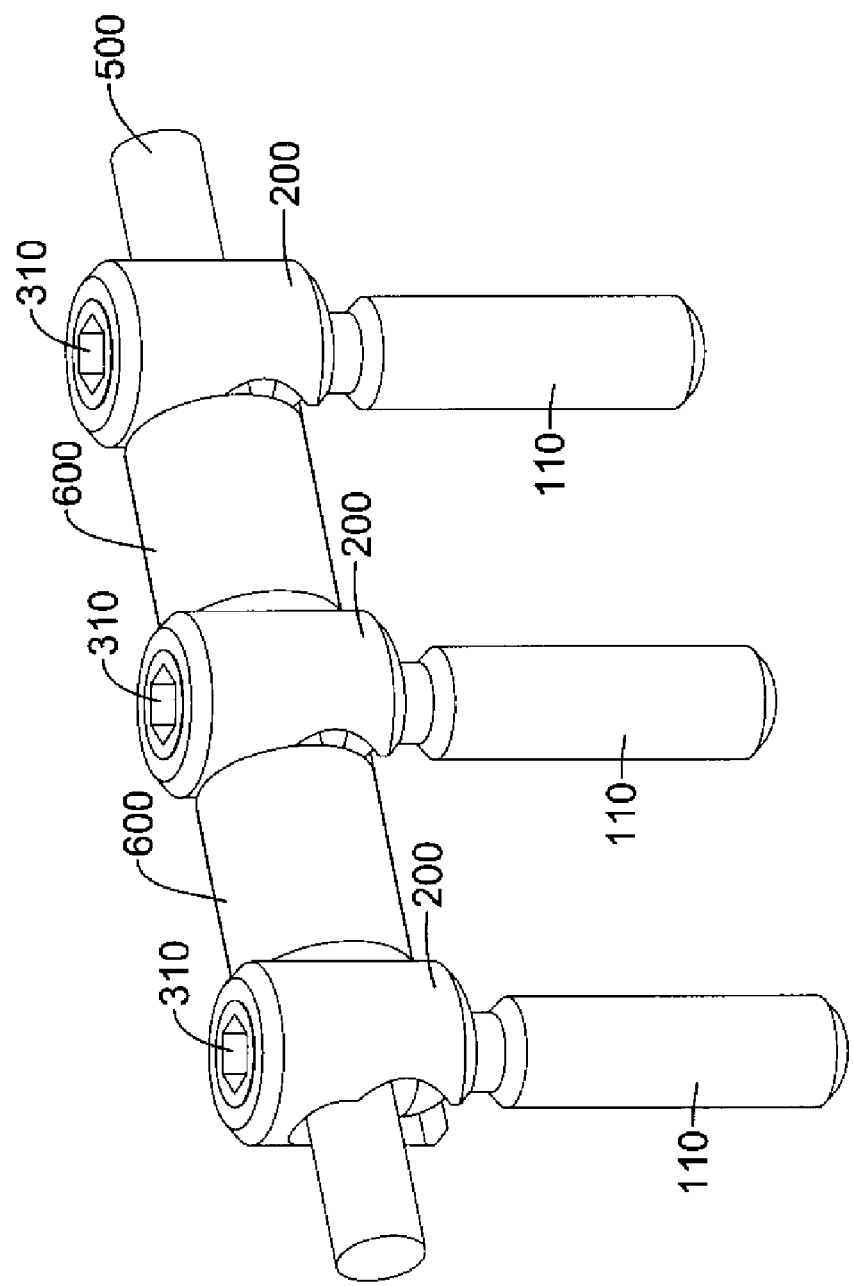
FIG. 15 is a perspective view of an embodiment of three bone anchors separated by spacers assembled on a cord.

In some embodiments, the longitudinal member 400 is a rod (FIG. 1). In other embodiments, the longitudinal member is a cord 500 (FIG. 15). When the longitudinal member is a cord 500, spacers 600 may be placed between the housings 200. In some embodiments, when implanted in a patient, the cord 500 may limit the range of flexion of the spine, whereas the spacer 600 may limit the range of extension of the spine. The cord 500 may be placed in tension and the spacer 600 may be placed in compression between the anchors 100. In use, the spacers 600 may be threaded onto the cord 500 between housings 200. The cord 500 and the spacer 600 may be formed, at least in part, of an elastomeric material. In one embodiment, the spacer is made of poly(carbonate urethane) (PCU), and the cord 500 is made of poly(ethylene terephthalate) (PET). The spacer 600 has an opening therethrough sized to receive the cord 500. The spacer 600 may be substantially cylindrical (FIG. 15), or have any other shape. In some embodiments, the cord 500 may be formed from one or more filaments or strands of an elastomeric material giving the cord 500 a degree of elasticity. In some instances, one or more elastomeric filaments or strands may be intermingled (e.g., woven, braided, knitted) with one or more inelastic, or relatively more inelastic filaments or strands. The cord 500 may be configured to have a variable stiffness through a range of displacement. For example, the stiffness of the cord may increase as an applied tensile force on the cord is increased. In some embodiments, the cord 500 may include a plurality of phases or regions of stiffness, for example, two, three, four, five, six or more phases of stiffness.

The anchor 100 (FIGS. 1-3) is connected to a longitudinal member 400 by a housing 200. The housing 200 has a first passage 205 that extends through the housing 200 from an upper opening 206 to a lower opening 207. The first passage 205 receives the anchor 100 and a fastener 300. The fastener 300 is configured to be received in the upper opening 206 and apply a force to the longitudinal member 400 and anchor 100. The fastener 300 can be a set screw, a pin, or any other structure that may be positioned in the first passage 205 to maintain the longitudinal member 400 in contact with the anchor 100. The shape of the outer surface of the fastener 300 and the inner surface of the first passage 205 at the upper opening 206 may be complementary. When the fastener 300 is a screw, it will be threaded to match threading in the first passage 205. Alternative complementary shapes may include grooves and ridges. The fastener 300 includes a tool recess 310 (FIGS. 2, 5), and may be cannulated for use with a cannulated anchor 100. A second passage 210 extends through the housing 200 transverse to the first passage 205. The second passage 210 receives the longitudinal member 400.

Figure 4:
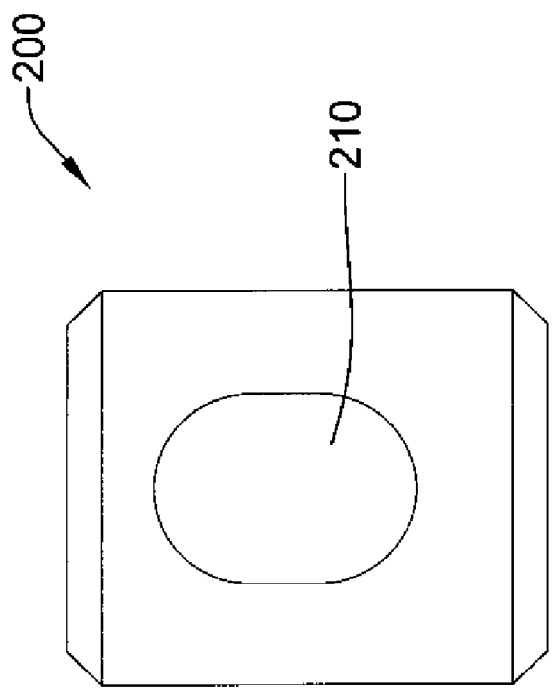
FIG. 4 is a rear view of the housing of FIG. 3.

The housing 200 has a side opening 215 sized and configured to receive the anchor head 130. The side opening 215 connects the second passage 210 and the lower opening 207 of the first passage 205 (FIGS. 1-3). The side opening 215 extends through one wall of the housing 200, in the front of the housing. FIG. 4 shows a rear view of the housing 200, with the second passage 210 extending all the way through the housing.

Figure 6:
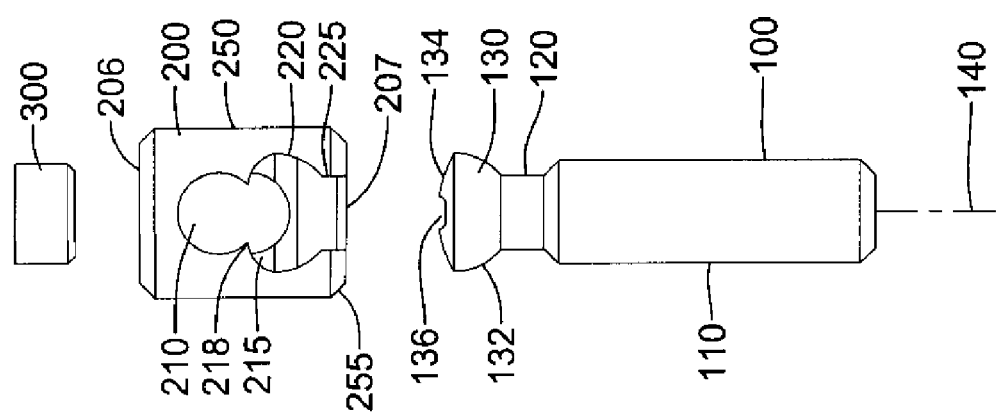
FIG. 6 is a front view of a bone anchor assembly in accordance with another embodiment of the invention.
Figure 7:
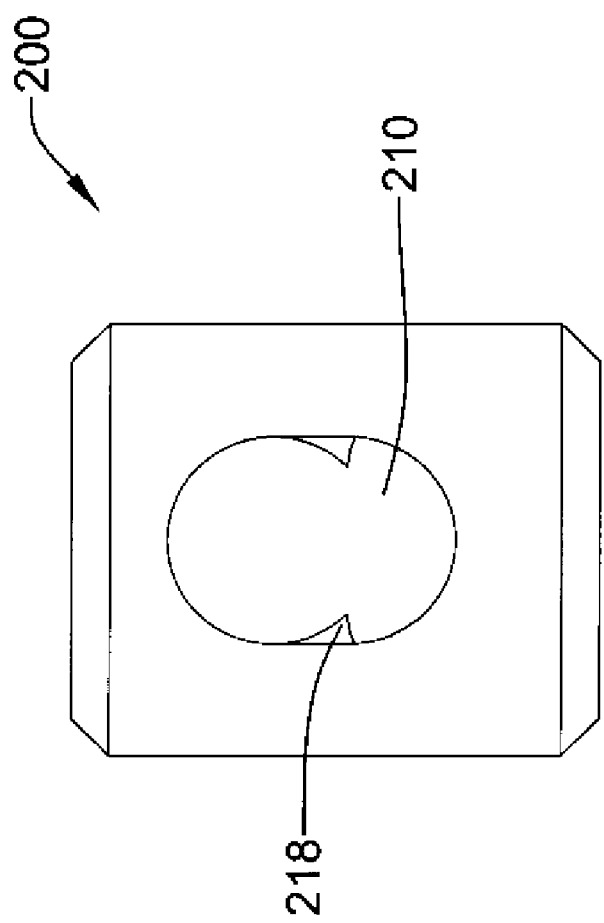
FIG. 7 is a rear view of the housing of FIG. 6.
Figure 8:
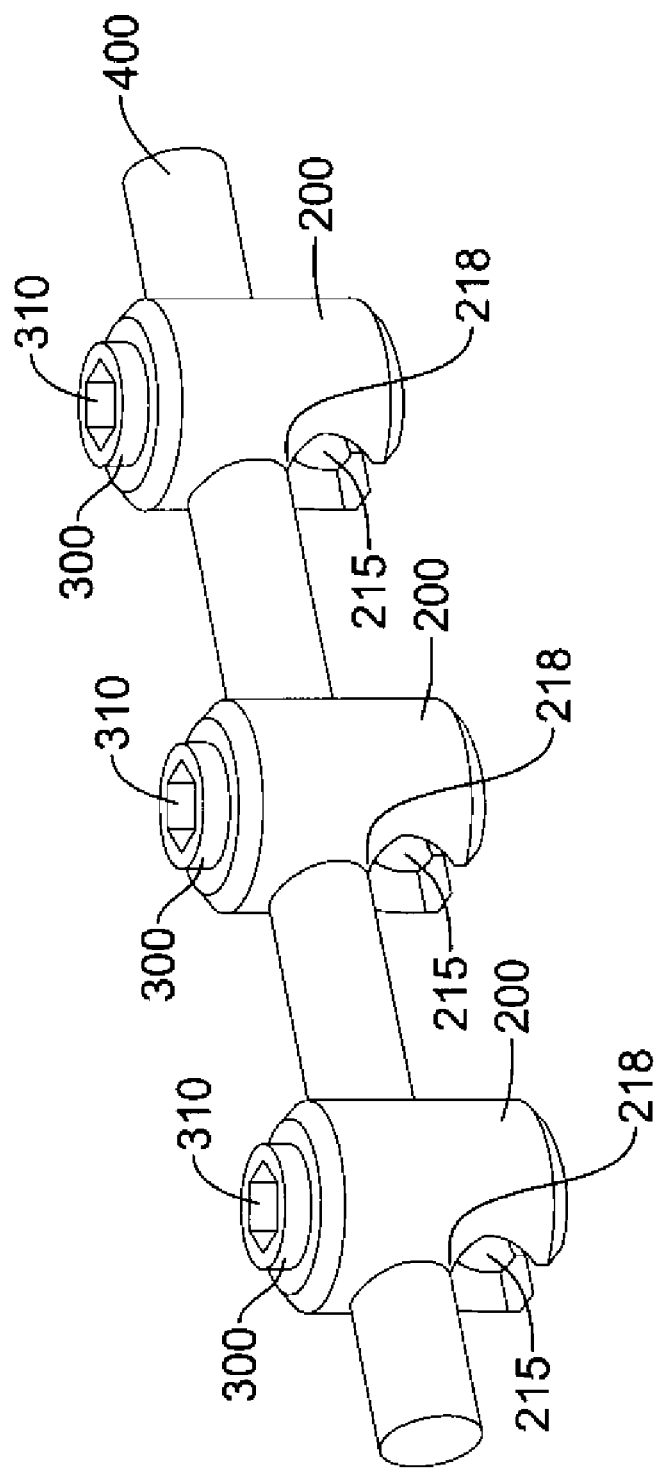
FIG. 8 is a perspective view of three housings according to FIG. 7 on a longitudinal member.

In one embodiment, the second passage 210 has a provisional capture mechanism including projections 218 (FIGS. 6-8). The projections 218 retain the longitudinal member 400 during insertion (FIG. 8). The projections 218 are configured to flex when the fastener 300 is advanced into the housing 200, allowing the longitudinal member 400 to move partially into the side opening 215 to contact the anchor head 130.

Figure 9:
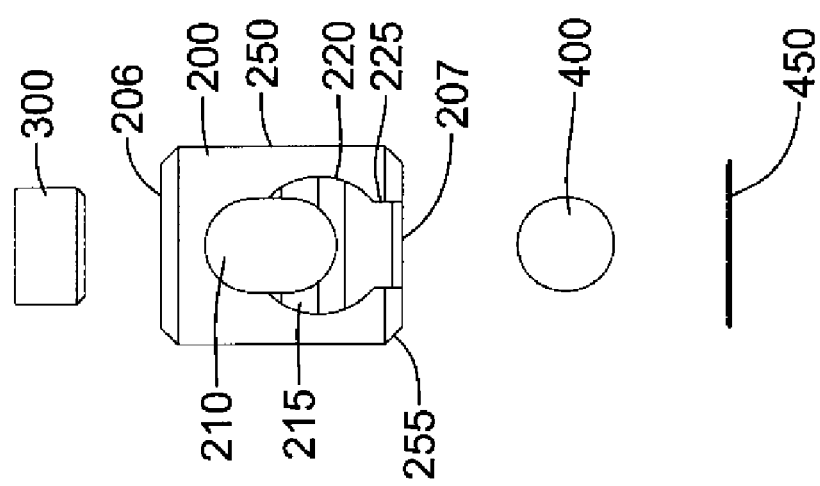
FIG. 9 is a front view of a bone anchor assembly in accordance with another embodiment of the invention.
Figure 10:
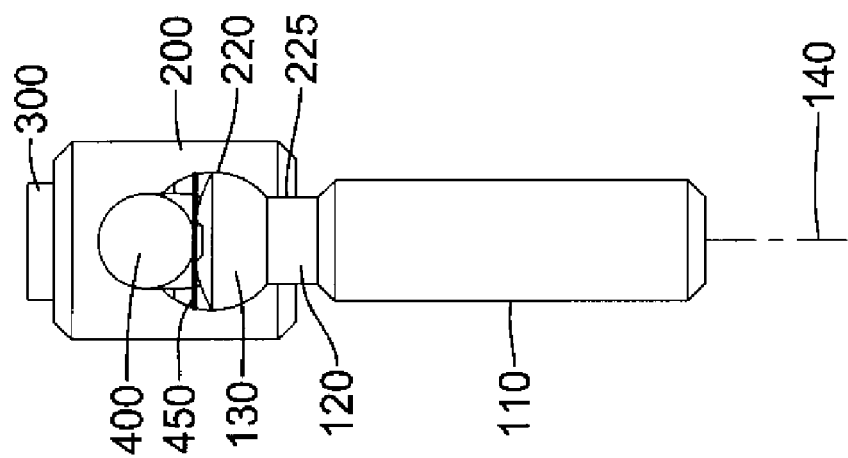
FIG. 10 is a front view of the bone anchor assembly of FIG. 9 assembled with an anchor.

In another embodiment, a retaining member 450 is positioned in the housing 200 to retain the longitudinal member 400 (FIGS. 9, 10). The retaining member 450 is sized and structured to have a friction fit within the housing 200. The retaining member 450 may be a polymer, metal, or other material providing a friction fit within the housing 200. The retaining member 450 may be resilient, compressible, or flexible. In some embodiments, the retaining member 450 is compressed between the longitudinal member 400 and the anchor head 130 when the fastener 300 is advanced into the housing 200, securing the anchor 100, longitudinal member 400 and housing 200 (FIG. 10).

The side opening 215 includes a first width 220 sized and configured to receive the anchor head 130, and a second width 225 sized and configured to receive the anchor neck 120 (FIG. 3). The first width 220 is greater than the second width 225. The first passage 205 in the housing 220 is defined by walls 250 including lower walls 255 adjacent the lower opening 207. The lower walls 255 angle inward toward the first passage 205, defining a tapered seat 260 configured to receive the bottom part spherical surface 132 of the anchor head 130. The shape of the seat 260 is complementary to the bottom part spherical surface 132 of the anchor head 130, resulting in an anchor 100 that is movable relative to the housing 200. The bottom part spherical surface 132 of the anchor head frictionally engages the seat 260 of the housing 200. The anchor 100 and the housing 200 are manually movable relative to each other by a surgeon when the longitudinal member is disengaged from the anchor 100. Accordingly, the anchor 100 is universally pivotable relative to the housing 200 so that the longitudinal axis 140 of the anchor 100 is positionable in any one of a plurality of angular positions relative to a longitudinal axis of the first passage 205.

Figure 13:
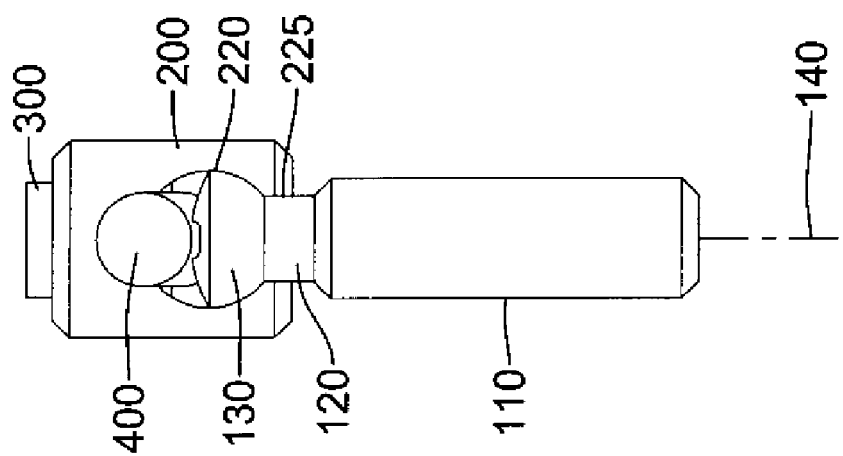
FIG. 13 is a front view of the bone anchor assembly of FIG. 12.

The size and shape of the side opening 215 at the first width 220 and second width 225 match the anchor head 130 and neck 120, respectively (FIGS. 3, 13). The bone anchor 100 is inserted into the side opening 215 with the anchor head 130 entering the side opening 215 at the first width 220 and the anchor neck 120 entering at the second width 225.

Figure 5:
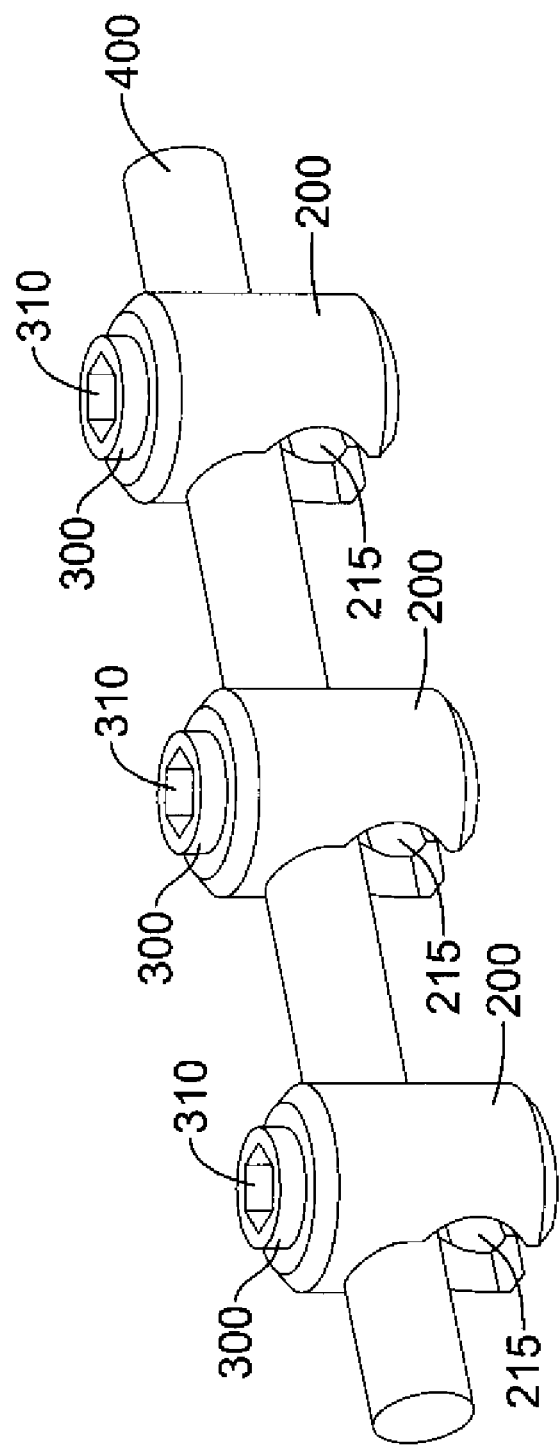
FIG. 5 is a perspective view of three housings on a longitudinal member.
Figure 11:
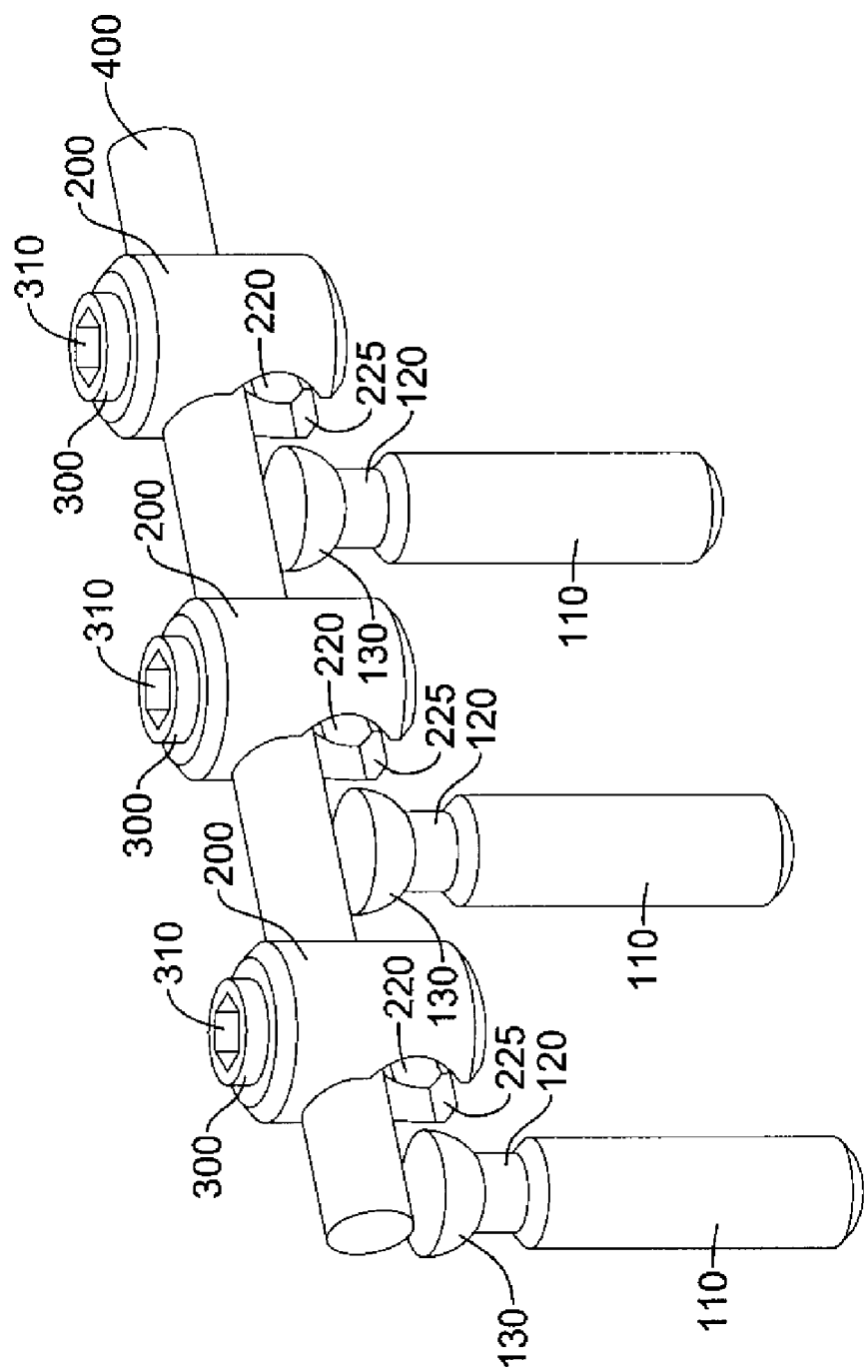
FIG. 11 is a perspective view of the housings of FIG. 5 positioned adjacent bone anchors.
Figure 12:
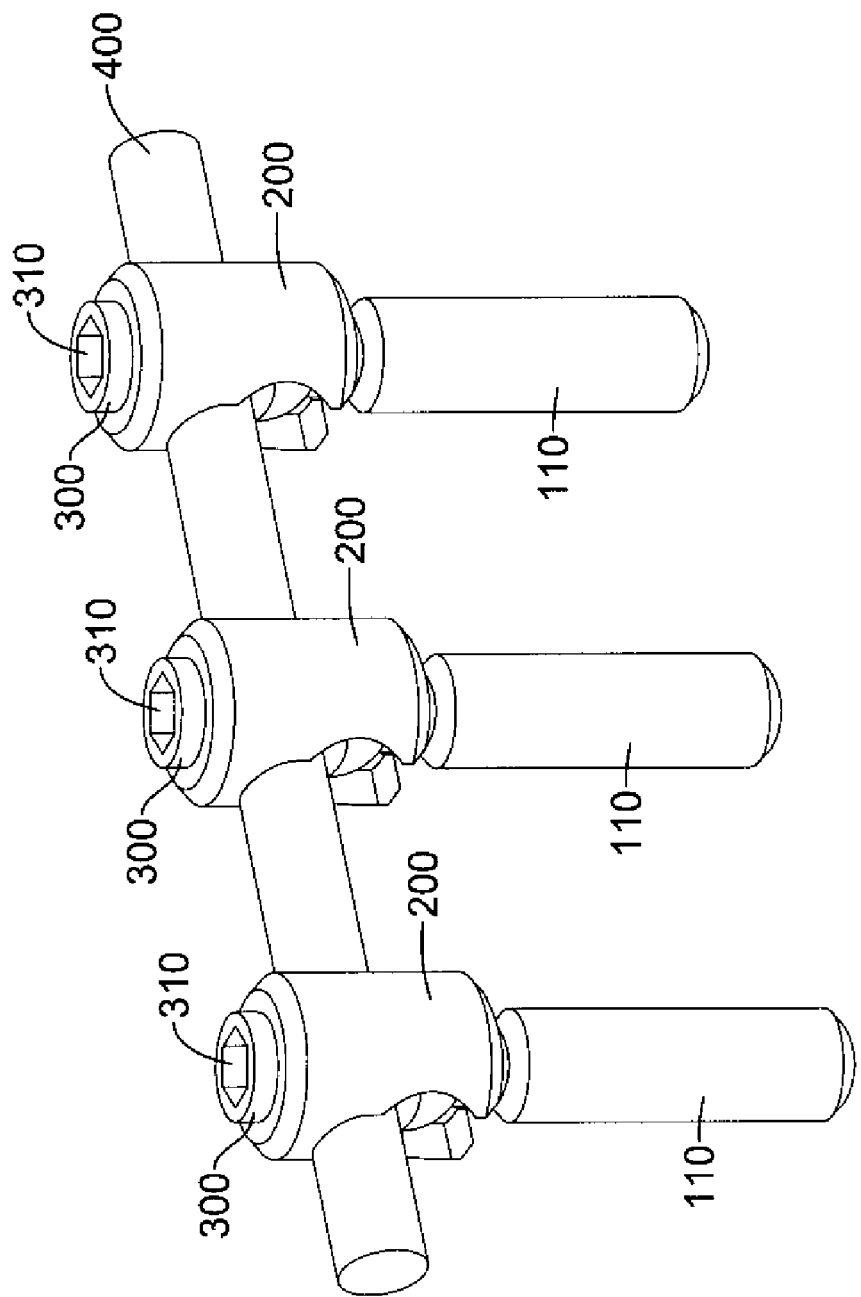
FIG. 12 is a perspective view of the housings of FIG. 11 positioned over the bone anchors.
Figure 14:
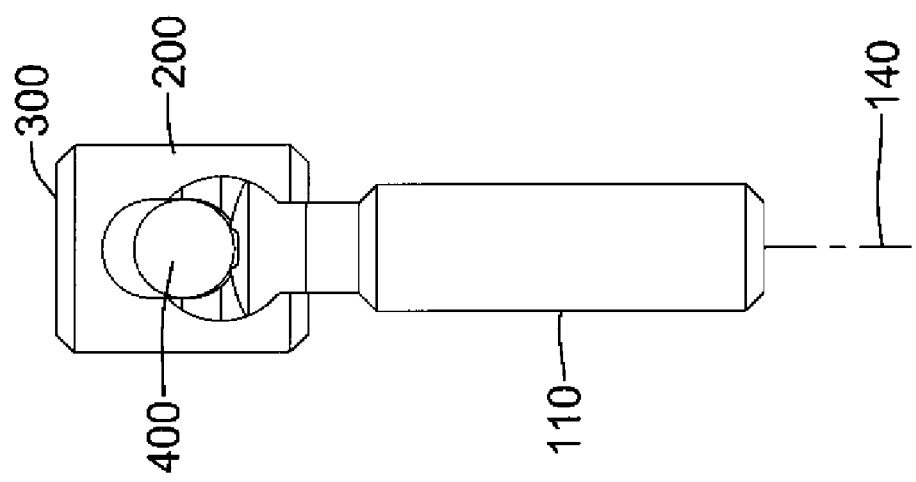
FIG. 14 is a front view of the bone anchor assembly of FIG. 13 with the housings secured to the bone anchors and longitudinal member.

In use, two or more anchors 100 are inserted into adjacent vertebrae. This may be accomplished percutaneously using a guidewire and cannulated anchors. In some applications, further dilation of the percutaneous access path is desired, and one or more dilators or obturators may be inserted over the guidewire to increase the size of the percutaneous access path. Once two or more anchors 100 are inserted into adjacent vertebrae, a longitudinal member 400 is inserted through the second passage 210 of two or more housings 200, and a fastener 300 is partially inserted into the upper opening 206 (FIG. 5). The longitudinal member 400 with attached housings 200 is positioned adjacent the anchors 100 (FIG. 11). The housings 200 are moved onto the anchors 100 with the first width 220 of the side opening 215 receiving the anchor head 130 and the second width 225 receiving the anchor neck 120 (FIGS. 12, 13). Once the housings 200 are positioned over the anchor heads 130, as shown in FIGS. 12 and 13, the housings 200 are lifted upwards to seat the bottom part spherical surface 132 of the anchor head 130 in the housing seat 260. This may be achieved by lifting the longitudinal member 400, which in turn, lifts the attached housings 200. Alternatively, each housing 200 can be lifted directly. The fasteners 300 are advanced into the upper opening 206, thereby moving the longitudinal member 400 into engagement with the anchor head 130 to secure the anchor 100, housing 200, and longitudinal member 400 (FIGS. 14, 15).

Prior to advancing the fasteners 300, each housing 200 may be pivoted on its respective anchor head 130 to a desired angle. In addition to the adjustment of angle between the anchor 100 and housing 200, the longitudinal member 400 may be bent to a desired angle prior to use. These adjustments allow for a wide variety of configurations for the anchor assembly.

Figure 16:
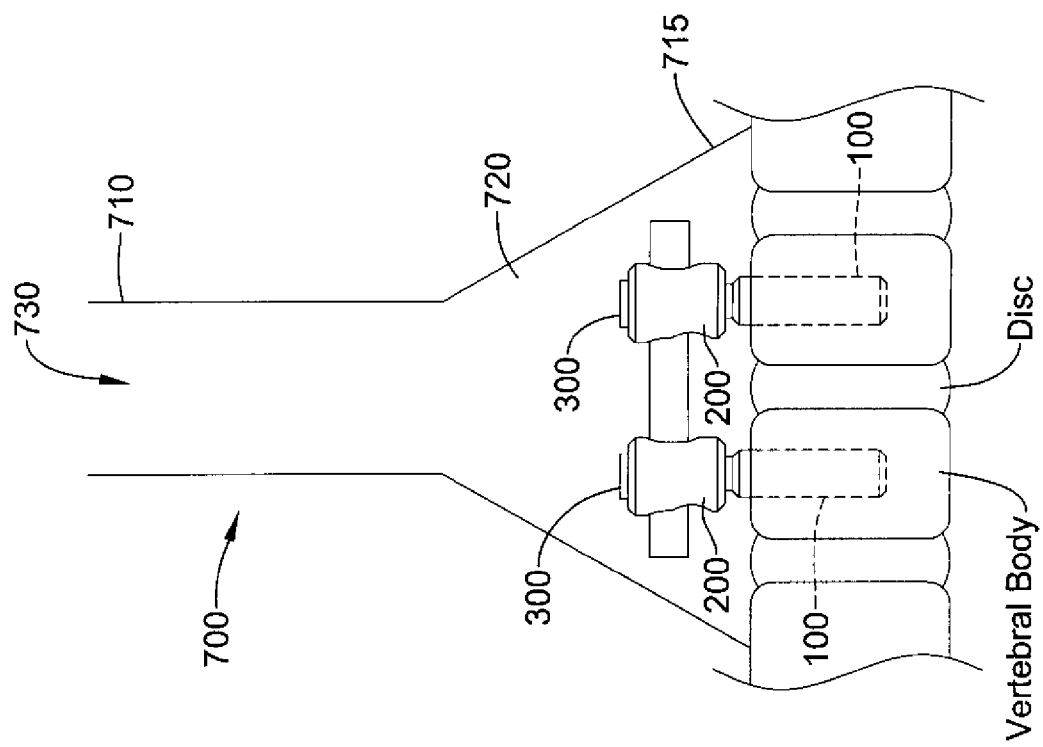
FIG. 16 is a schematic illustration of a surgical procedure performed through an access device.

In one method, after an incision is made, the tissue may be dilated, and an access device 700 or a retractor may be inserted over the dilator (or obturator). The access device may be used to enclose one or more of the adjacent vertebrae in a working space at the target site so that a minimally invasive portion of a procedure may be performed (FIG. 16). In some embodiments, the access device has a proximal end 710 and a distal end 715 and a path 730 extending therebetween. The access device may also have an expandable distal portion 720 that may be expanded so that the distal portion 720 extends over one or more adjacent vertebrae, allowing the insertion of multiple anchors 100 and a longitudinal member 400 through a single access device 700 (FIG. 16). In some embodiments, the distal portion 720 of the access device 700 expands to provide access to three vertebrae, allowing for a three-level procedure to be performed through a single access device.

A method of using a single access device 700 to insert two anchors 100 and a longitudinal member 400 involves inserting the access device 700 through a first incision in the skin of the patient and advancing the access device until the distal end 715 is adjacent first and second vertebral target sites (FIG. 16). The distal portion 720 of the access device is expanded, and two anchors 100 are passed through the access device 700 and secured to the patient's vertebrae at the first and second target sites. A longitudinal member 400 is inserted through two housings 200, and then inserted through the access device 700 until a distal end of the longitudinal member 400 is adjacent the first target site. The distal end of the longitudinal member 400 is then advanced to the second target site until a proximal end of the longitudinal member 400 is adjacent the first target site, and each housing 200 is adjacent an anchor head 130. The housings 200 are slid onto the anchor heads 130, with the anchor heads 130 entering the side openings 215 on the housings 200. The housings 200 and longitudinal member 400 are then secured to the anchors 100 (FIG. 16).

In another embodiment, retaining members 450 are inserted into each housing 200 to retain the longitudinal member 400 as it is inserted through the access device 700. The retaining member 450 can be inserted through the upper opening 206 or the lower opening 207 in the housing 200. Once the longitudinal member 400 is inserted through the second passage 210, the position of the retaining member 450 can be adjusted to secure the housing 200 on the longitudinal member 400.

In other embodiments, two or more access devices may be inserted at two or more adjacent vertebral sites. In some embodiments anchors are inserted into two or more vertebrae and one or more longitudinal members are attached to the anchors spanning multiple vertebrae. The anchors and longitudinal member may be inserted through a single access device (FIG. 16). In other embodiments, multiple access devices may be used. When two or more access devices are used, the longitudinal member may be inserted through an incision between the access devices that extends from the skin to the target sites adjacent the spine. In other methods, a pathway or tunnel is created beneath the skin, between adjacent target sites. The longitudinal member is inserted through one access device and pushed or pulled through the pathway into position for attachment to multiple anchors in the adjacent vertebrae. The creation of a tissue pathway allows for the insertion of anchors and a longitudinal member through the original percutaneous paths, without additional incisions or tissue trauma.

It is appreciated that many variations of this method are possible and that the actions described herein can be performed in many ways and in many orders so as to enable access to the vertebral sites. For example, a two-level procedure may involve delivering three anchors to three adjacent vertebral sites using two or three access devices.

Some example structures and/or configurations of access devices that can be used with the methods disclosed herein are disclosed in U.S. patent application Ser. No. 11/760,537, filed Jun. 8, 2007, published as Publication No. U.S. 2007/0299443 A1, U.S. patent application Ser. No. 10/926,579, filed Aug. 26, 2004, published as Publication No. U.S. 2005/0273131 A1, U.S. patent application Ser. No. 10/927,633, filed Aug. 26, 2004, now U.S. Pat. No. 7,179,225, U.S. patent application Ser. No. 10/845,389, filed May 13, 2004, published as Publication No. 2004/0230100 A1, U.S. patent application Ser. No. 10/658,736, filed Sep. 9, 2003, published as Publication No. 2004/0133201 A1, which are all hereby expressly incorporated by reference herein in their entireties.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method of treating the spine of a patient, the method comprising:
   inserting two or more anchors into a plurality of adjacent vertebrae, each anchor having a head and a shaft;
   providing a housing for each anchor, each housing having a first passage extending longitudinally therethrough between an upper opening and a lower opening, a second passage transverse to the first passage and configured to receive a longitudinal member, and a side opening configured to receive the anchor head;
   sliding two or more housings onto a longitudinal member, the longitudinal member configured to extend through the second passages in the housings;
   positioning the longitudinal member with the two or more housings disposed thereon adjacent the anchors such that each housing is adjacent an anchor head;
   sliding the housings onto the anchor heads with the anchor heads being received in the side openings; and
   securing the housings and longitudinal member to the anchor heads;
   wherein the anchor has a neck between the head and shaft, the neck having a width smaller than a width of the head, wherein the side opening in the housing includes a first width configured to receive the anchor head and a second width configured to receive the anchor neck, wherein sliding the housings onto the anchor heads includes positioning each housing such that the first width is aligned with the anchor head and the second width is aligned with the anchor neck.

2. The method of claim 1, wherein the housings are translatable on the longitudinal member.

3. The method of claim 1, further comprising inserting a retaining member into each housing, the retaining member retaining the housing on the longitudinal member.

4. The method of claim 1, wherein securing the housings includes advancing fasteners through the upper opening in each housing.

5. The method of claim 4, wherein advancing the fasteners moves the longitudinal member toward the anchor head and lifts the housing axially away from the anchor head.

6. The method of claim 1, wherein the side opening is continuous with the second passage on one side of the housing, wherein securing the housings to the anchor heads includes moving the longitudinal member at least partially into the side opening.

7. The method of claim 1, comprising inserting three or more anchors into three or more vertebrae and sliding three or more housings onto the longitudinal member.

8. The method of claim 1, wherein the longitudinal member is a cord.

9. The method of claim 8, wherein sliding two or more housings onto a longitudinal member includes sliding a first housing onto the cord, sliding a spacer onto the cord, and sliding a second housing onto the cord.

10. A method of treating the spine of a patient, the method comprising:
    inserting two or more anchors into a plurality of adjacent vertebrae, each anchor having a head and a shaft;
    providing a housing for each anchor, each housing having a first passage extending longitudinally therethrough between an upper opening and a lower opening, a second passage transverse to the first passage and configured to receive a longitudinal member, and a side opening configured to receive the anchor head;
    sliding two or more housings onto a longitudinal member, the longitudinal member configured to extend through the second passages in the housings;
    positioning the longitudinal member with the two or more housings disposed thereon adjacent the anchors such that each housing is adjacent an anchor head;
    sliding the housings onto the anchor heads with the anchor heads being received in the side openings; and
    securing the housings and longitudinal member to the anchor heads;
    wherein the housing has a seat formed by walls of the housing at the lower opening being tapered toward the first passage, the seat configured to receive a bottom surface of the anchor head and prevent the anchor from moving laterally out of the housing, wherein securing the housings includes moving the housing axially away from the anchor to position the anchor head in the seat.

11. The method of claim 10, wherein the seat and the bottom surface of the anchor head are part spherical, wherein after sliding the housings onto the anchor heads, the method further comprises tilting the housing to adjust an angle of the housing relative to the anchor to achieve a desired orientation of the longitudinal member.

12. A method for treating the spine of a patient, the method comprising:
    advancing at least one access device through a first incision in the skin of the patient, the access device having a proximal end and a distal end and a path extending therebetween, advancing the access device until the distal end is adjacent at least first and second vertebral target sites;
    inserting two or more anchors along the path through the access device and securing the anchors to the patient's vertebrae at the first and second vertebral target sites, each anchor having a head and a shaft, the shaft being secured to the vertebra;
    providing a longitudinal member and two or more housings, the longitudinal member configured for insertion through the two or more housings, each housing having a first passage extending longitudinally therethrough between an upper opening and a lower opening, a second passage transverse to the first passage and configured to receive the longitudinal member, and a side opening configured to receive the anchor head;
    inserting the longitudinal member with housings disposed thereon through the access device until a distal end of the longitudinal member is adjacent the first target site;
    advancing the distal end of the longitudinal member to the second target site, until a proximal end of the longitudinal member is adjacent the first target site, the distal end of the longitudinal member is adjacent the second target site, and each housing is adjacent an anchor head;
    sliding each housing onto an anchor head such that the anchor head enters the side opening; and
    securing the housings and longitudinal member to the anchor heads.

13. The method of claim 12, further comprising inserting a retaining member into each housing, the retaining member retaining the housing on the longitudinal member.

14. The method of claim 12, further comprising inserting a second access device through a second incision in the skin of the patient, the second access device having a second proximal end and a second distal end and a second path extending therebetween, advancing the second access device until the second distal end is adjacent the second target site;
    wherein at least one anchor is passed through each access device.

15. The method of claim 14, wherein after the anchors are secured to the vertebrae, the method further comprises creating a pathway under the skin from the first target site to the second target site, wherein the longitudinal member is inserted through one access device and advanced through the pathway to the second target site.

16. The method of claim 12, wherein the anchor has a neck between the head and shaft, the neck having a width smaller than a width of the head, wherein the side opening in the housing includes a first width configured to receive the anchor head and a second, smaller width configured to receive the anchor neck, wherein sliding the housings onto the anchor heads includes positioning each housing such that the first width is aligned with the anchor head and the second width is aligned with the anchor neck.

17. The method of claim 12, wherein the housings have a seat at the lower opening configured to receive a bottom surface of the anchor head and configured to prevent the anchor from moving laterally out of the housing when the anchor head is seated in the seat, wherein securing the housings includes moving the housing axially away from the anchor to position the anchor head in the seat.

18. The method of claim 17, wherein moving the housing axially away from the anchor is achieved by advancing a fastener into the upper opening in the housing, the fastener contacting and moving the longitudinal member into contact with the anchor head.

19. The method of claim 12, wherein the side opening is continuous with the second passage on one side of the housing, wherein securing the housings to the anchor heads includes moving the longitudinal member at least partially into the side opening.

20. The method of claim 12, comprising inserting three or more anchors through the at least one access device into three or more vertebrae and sliding three or more housings onto the longitudinal member.

21. The method of claim 12, wherein the longitudinal member is a rod.

22. The method of claim 12, wherein the longitudinal member is a cord.

23. The method of claim 22, wherein inserting a longitudinal member through two or more housings includes sliding a first housing onto the cord, sliding a spacer onto the cord, and sliding a second housing onto the cord.

* * * * *